(12) United States Patent  (10) Patent No.: US 7,428,320 B2
Northcott et al.  (45) Date of Patent: *Sep. 23, 2008

(54) IRIS IMAGING USING REFLECTION FROM THE EYE

(75) Inventors: Malcolm J Northcott, Felton, CA (US); J. Elon Graves, Los Gatos, CA (US)

(73) Assignee: AOptix Technologies, Inc., Campbell, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/297,578

(22) Filed: Dec. 7, 2005

(65) Prior Publication Data

US 2006/0140454 A1  Jun. 29, 2006

Related U.S. Application Data

(60) Provisional application No. 60/654,638, filed on Feb. 17, 2005, provisional application No. 60/634,331, filed on Dec. 7, 2004.

(51) Int. Cl.
*G06K 9/00* (2006.01)
(52) U.S. Cl. ............... 382/117; 351/220; 351/221; 356/71; 382/190
(58) Field of Classification Search ........... 382/117, 382/118, 115, 291, 190, 124; 351/205, 206, 351/221, 207, 212, 219, 246, 220; 348/78, 348/335, 344, 346; 606/4; 359/210, 466; 356/71
See application file for complete search history.

(56) References Cited

U.S. PATENT DOCUMENTS

| 5,956,122 | A  | * | 9/1999  | Doster ................. 351/210 |
| 6,095,651 | A  | * | 8/2000  | Williams et al. ...... 351/246 |
| 6,099,522 | A  | * | 8/2000  | Knopp et al. ......... 606/10 |
| 6,252,977 | B1 | * | 6/2001  | Salganicoff et al. ... 382/117 |
| 6,439,720 | B1 |   | 8/2002  | Graves et al. |
| 6,447,119 | B1 | * | 9/2002  | Stewart et al. ........ 351/212 |
| 6,452,145 | B1 |   | 9/2002  | Graves et al. |
| 6,464,364 | B2 |   | 10/2002 | Graves et al. |
| 6,609,794 | B2 | * | 8/2003  | Levine ................ 351/221 |
| 6,721,510 | B2 |   | 4/2004  | Graves et al. |
| 6,922,250 | B2 | * | 7/2005  | Fercher ............... 356/497 |
| 2003/0226978 | A1 | * | 12/2003 | Ribi et al. .......... 250/474.1 |

* cited by examiner

*Primary Examiner*—Sheela C Chawan
(74) *Attorney, Agent, or Firm*—Fenwick & West LLP

(57) ABSTRACT

A rapid iris acquisition, tracking, and imaging system can be used at longer standoff distances and over larger capture volumes, without the active cooperation of subjects. The captured iris images can be used for biometric identification. Light illuminates the subjects' eyes. Eye reflection from the eyes is used to steer a high resolution camera to the eyes in order to capture images of the irises.

65 Claims, 5 Drawing Sheets

IRIS IMAGING USING REFLECTION FROM THE EYE

CROSS-REFERENCE TO RELATED APPLICATION(S)

This application claims priority under 35 U.S.C. § 119(e) to U.S. Provisional Patent Application Ser. No. 60/654,638, "Biometric Identification and Iris Imaging Using Retinal Retro-Reflection," filed Feb. 17, 2005; and to U.S. Provisional Patent Application Ser. No. 60/634,331, "Adaptive Optics (AO) Imaging Applied to Biometric Identification Using Iris Imaging," filed Dec. 7, 2004. The subject matter of all of the foregoing is incorporated herein by reference in their entirety.

BACKGROUND OF THE INVENTION

1. Field of the Invention

This invention relates to imaging of the human iris, as may be used for biometric identification.

2. Description of the Related Art

As traditional forms of personal identification become vulnerable to advancing technology, biometric identification is increasingly seen as a viable approach to personal identification. Techniques such as voice recognition, fingerprinting, and iris imaging rely on physical personal traits that are difficult to change or duplicate.

However, biometric identification via iris imaging typically requires a high resolution image of the iris in order to resolve the fine details necessary to make a positive identification. An image of an iris with approximately 200 micron or better spatial resolution typically is required to uniquely distinguish the fine muscle structure of human irises, as may be required for identification purposes. In systems where the subject is actively cooperating, conditions such as illumination geometry, camera resolution, exposure time, and wavelength of light can be optimized in order to capture a high contrast image of the fine structure of the iris. Existing systems typically require a subject to hold his head in a specific position while staring at the iris imaging camera from close proximity and at a nearly head-on aspect. Although recent advances have been made in iris imaging, the task of capturing sufficiently high resolution images of the human iris generally still requires a fair degree of active cooperation from the subject.

For example, a system using commercial color CCD technology (e.g., 5 megapixels) would typically have a field of view of approximately 15 cm at a 1 m standoff range, yielding a spatial resolution of approximately 75 microns per pixel at the 1 m standoff range. Thus, the subject would have to be within approximately 1 m of the camera and would have to position his iris within the 15 cm field of view for a long enough period of time in order for the camera to focus and capture an adequate resolution image of the iris. This typically requires the subject's active cooperation. The situation becomes significantly worse at longer standoffs. For example, if the same camera were used at a standoff of 10 m, maintaining the same angular resolution would result in a spatial resolution of 750 µm per pixel, which is unacceptable. On the other hand, maintaining a spatial resolution of 75 µm per pixel would result in a 15 cm wide field of view at 10 m. Keeping the iris within this field of view is also very difficult.

The "capture volume" of an iris imaging system is the volume over which the iris imaging system can capture iris images of sufficiently high resolution. The CCD-based system described above and other similar traditional systems have a small capture volume—so small as to make traditional iris imaging systems unsuitable for use in uncooperative situations, such as iris imaging over large groups of people, over longer standoff distances, or for covert identification applications. For example, it may be desirable to capture iris images of subjects as they walk through a portal, such as a metal detector, or in places like airports, train stations, border crossings, secure building entrances and the like. The high-resolution and longer standoff requirements in these applications place significant challenges on iris imaging systems that cannot be met by current designs. The capture volume and standoff capabilities of current iris imaging systems are not large enough to efficiently address these types of situations.

Therefore, there is a need for iris imaging systems that have larger capture volumes and/or can be used at longer standoff distances.

SUMMARY OF THE INVENTION

The present invention overcomes the limitations of the prior art by providing a rapid iris imaging system that can be used at longer standoff distances and over larger capture volumes, without the active cooperation of subjects. Light illuminates the subjects' eyes. Reflection from the eyes (e.g., retro-reflection from the retina or glint reflection from the cornea) is used to steer (and preferably also focus) a high resolution camera to the eyes in order to capture images of the irises. Real-time steering and focus correction may extend the usable exposure time, thus allowing good images under lower illumination levels than otherwise possible. Other methods may also be envisaged for real-time control of steering and focus.

In one embodiment, the iris imaging system includes an imaging subsystem. The imaging subsystem includes a camera, a light source and a fine tracking system. The camera captures images of irises with sufficient resolution for biometric identification. The light source produces light that illuminates eyes within a capture volume. The fine tracking system steers the camera to eyes, based on a reflection from the eyes, preferably either a retro-reflection or a glint reflection.

In one approach, the fine tracking system includes an adaptive optics loop that is driven by the reflected light. For example, the adaptive optics loop can include a deformable mirror, a wavefront sensor and a controller. The wavefront sensor senses the wavefront of the reflected light and a controller drives the deformable mirror based on the sensed wavefront. The deformable mirror corrects the incoming wavefront, thus steering the camera to the eye (i.e., correction of tip and tilt wavefront errors). The deformable mirror may also focus the camera (i.e., correction of focus-error). In this way, the imaging subsystem can acquire iris images, even without the subject's active cooperation.

The iris imaging system may also include an acquisition subsystem that identifies the approximate location of subjects within a capture volume. For example, a wide field of view acquisition subsystem may be coupled with a narrower field of view imaging subsystem. The acquisition subsystem identifies the approximate location of subjects, and the imaging subsystem slews from one subject to the next to acquire images of their irises. A controller coordinates the two subsystems. In one approach, the acquisition subsystem identifies the approximate location of subjects based on retro-reflections from the subjects' eyes. This is convenient since the circular shape of the eye pupil allows one to easily distinguish retro-reflections from the eye from other light sources. The two subsystems may be partially or fully integrated. For example, they may be optically aligned so that they are both looking in the same general direction, although the acquisition subsystem typically will have a much larger field of view than the imaging subsystem.

Other aspects of the invention include methods corresponding to the devices and systems described above.

BRIEF DESCRIPTION OF THE DRAWINGS

The invention has other advantages and features which will be more readily apparent from the following detailed description of the invention and the appended claims, when taken in conjunction with the accompanying drawings, in which:

The figures depict embodiments of the present invention for purposes of illustration only. One skilled in the art will readily recognize from the following discussion that alternative embodiments of the structures and methods illustrated herein may be employed without departing from the principles of the invention described herein.

DETAILED DESCRIPTION OF THE PREFERRED EMBODIMENTS

Figure 1:
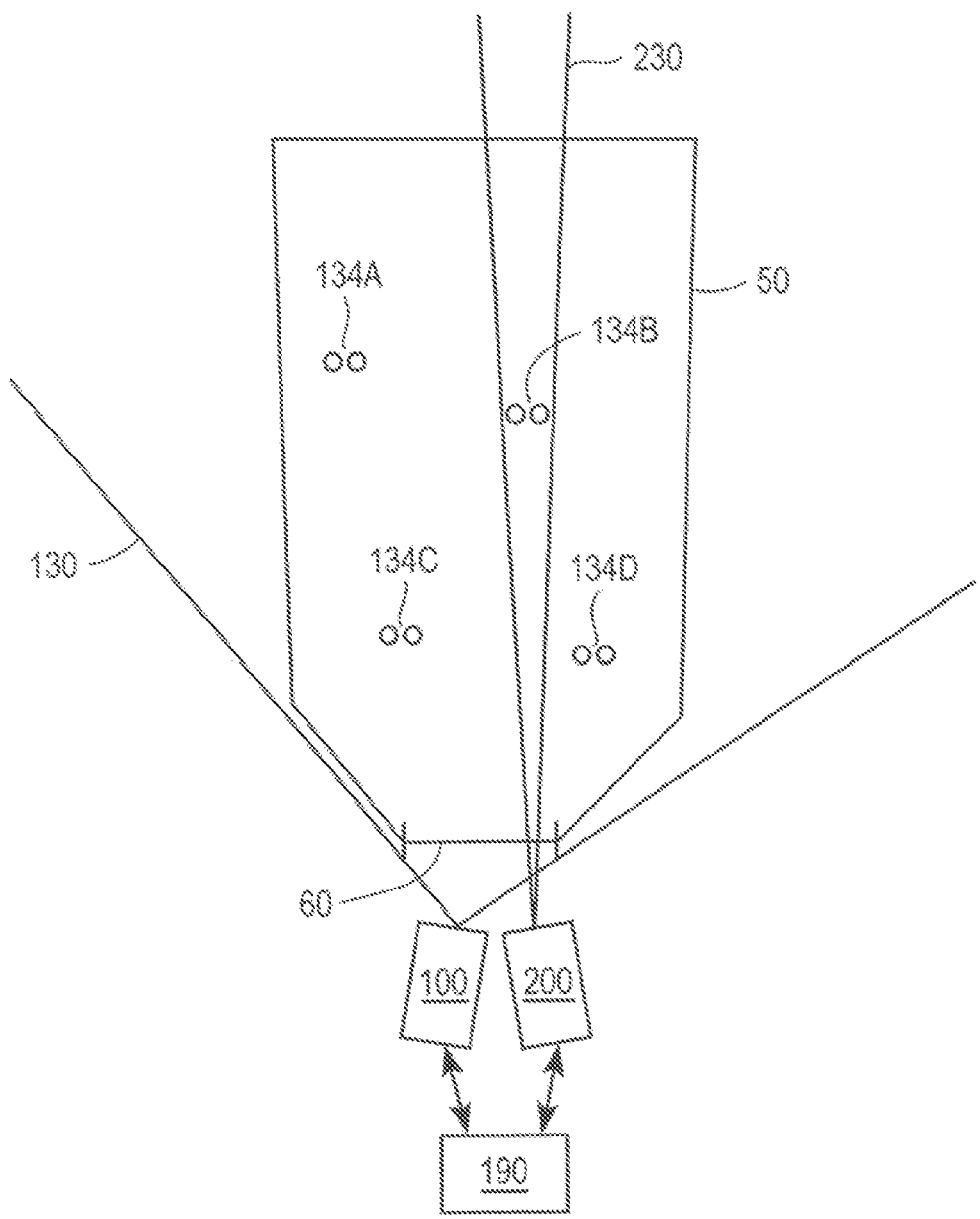
FIG. 1 is an illustration of an iris imaging system according to the present invention.

FIG. 1 is an illustration of an iris imaging system according to the present invention. The iris imaging system includes an imaging subsystem 200 and, optionally, an acquisition subsystem 100. The system is designed to capture iris images of many eyes 134 over a large capture volume 50, typically without the active cooperation of the subjects. In one application, the subjects are passing through a portal 60 (such as a doorway or metal detector), the capture volume 50 is the entranceway leading up to the portal, and the iris imaging system captures iris images as the subjects pass through the capture volume. In many applications, the capture volume can be defined based on a portal or other bottleneck for the flow of people. Examples include corridors, turnstyles, toll booths, elevator doors, escalators and parking garage entrances. Other examples include checkout lines or other queues, crosswalks, sidewalks and roadways.

This situation typically is "uncooperative," meaning that the subjects are not actively cooperating in the iris imaging. For example, they are not placing their heads into a device to allow capture of iris images. Rather, they are simply walking through the portal and the system captures their iris images as they do so. They may even be unaware that the system is doing so. If stealth is important, the wavelengths should be chosen to be non-visible.

The imaging subsystem 200 captures the iris images for each subject. However, in order to obtain sufficient resolution in the iris image, the imaging subsystem 200 has a fairly narrow field of view 230. Therefore, in order to cover the entire capture volume, the imaging subsystem 200 is actively steered from one subject to the next. Coarse tracking of subjects can be achieved in many different ways. In FIG. 1, an acquisition subsystem 100 with a wide field of view 130 is used to identify the approximate location of each subject. This information is used to coarsely steer the imaging subsystem 200 to the general vicinity of the subject. Once in the general vicinity, fine tracking is achieved by illuminating the subject's eye with an optical beam and steering the imaging subsystem 200 to the eye based on a reflection from the subject's eye. Examples of eye reflections include retro-reflection from the retina and glint reflection from the corneal surface. The eye reflection can also be used to focus the imaging subsystem 200 on the iris to capture the high resolution image. The tracking (and focus) occurs fairly rapidly in real-time if a large capture volume and throughput of subjects is to be accommodated.

Different devices can be used for the acquisition subsystem 100 and for the imaging subsystem 200. The acquisition subsystem 100 can also be based on tracking subjects using reflection from their eyes. Alternately, it can be based on completely different mechanisms. For example, the acquisition subsystem 100 might capture conventional digital images of the capture volume. Software is then used to identify which parts of each captured image represent humans and/or which part of each human is his face or eyes. Frame to frame comparisons can be used to track movement of subjects. Stereoscopic systems (based on eye reflection, conventional imaging or other approaches) can be used to triangulate subject positions within the capture volume.

In FIG. 1, the acquisition subsystem 100 is shown as a single box with a wide field of view 130. This is merely a representation. The acquisition subsystem 100 is not limited to a single box. In the stereoscopic example, equipment is positioned at different locations in order to capture different viewpoints. Even if a stereoscopic approach is not used, multiple cameras can still be used advantageously, for example to more efficiently cover the entire capture volume 50.

The wide field of view 130 also need not be implemented literally as shown in FIG. 1. Each acquisition camera(s) may have a wide field of view that covers the entire capture volume 50, as shown in FIG. 1. Alternately, each acquisition camera may cover less than the entire capture volume 50, but the cameras together cover the entire capture volume 50. In addition, the cameras may be scanning rather than staring and their instantaneous fields of view may be smaller than the capture volume 50. At any instant in time, only a fraction of the entire capture volume is covered but, over time, the entire capture volume is covered.

As a final example, the acquisition subsystem 100 may not be based on cameras at all. Other types of position sensors or intrusion sensors may be used to determine the location of subjects. For example, the capture volume 50 may be covered by a grid of light beams. The position of subjects is determined by the subjects' breaking the light beams. In a different approach, floor mounted pressure pads may be used to determine subject positions. Sonar, radar, lidar, and thermal detection or imaging are examples of other technologies that can be used to determine subject positions. For certain types of sensors, the term "field of view" may not even be applicable, so long as the acquisition subsystem 100 is sufficient to cover the capture volume 50.

Controller 190 coordinates the two subsystems. The information from the acquisition subsystem 100 is used by the imaging subsystem 200 (via controller 190) to coarsely steer the narrow field of view 230 from subject to subject. As with the acquisition subsystem 100, many different designs for the imaging subsystem 200 are also possible. In one approach, conventional devices such as steering mirrors or gimbals are used to coarsely steer the narrow field of view 230 to the subject 134. An adaptive optics system (not shown in FIG. 1) is then used to achieve fast, fine tracking of the subject 134 and optionally also focus adjustment for the image capture. The adaptive optics system is driven by the eye reflection from the subject's eye 134 and/or by other position and distance measurement techniques. Other approaches can also be used. Risley prisms, liquid crystal phased arrays, real time holograms and Bragg gratings are examples of other steering devices. Other signal sources could include glints, parallax using images or eye reflections, and time of flight lidar.

Figure 2:
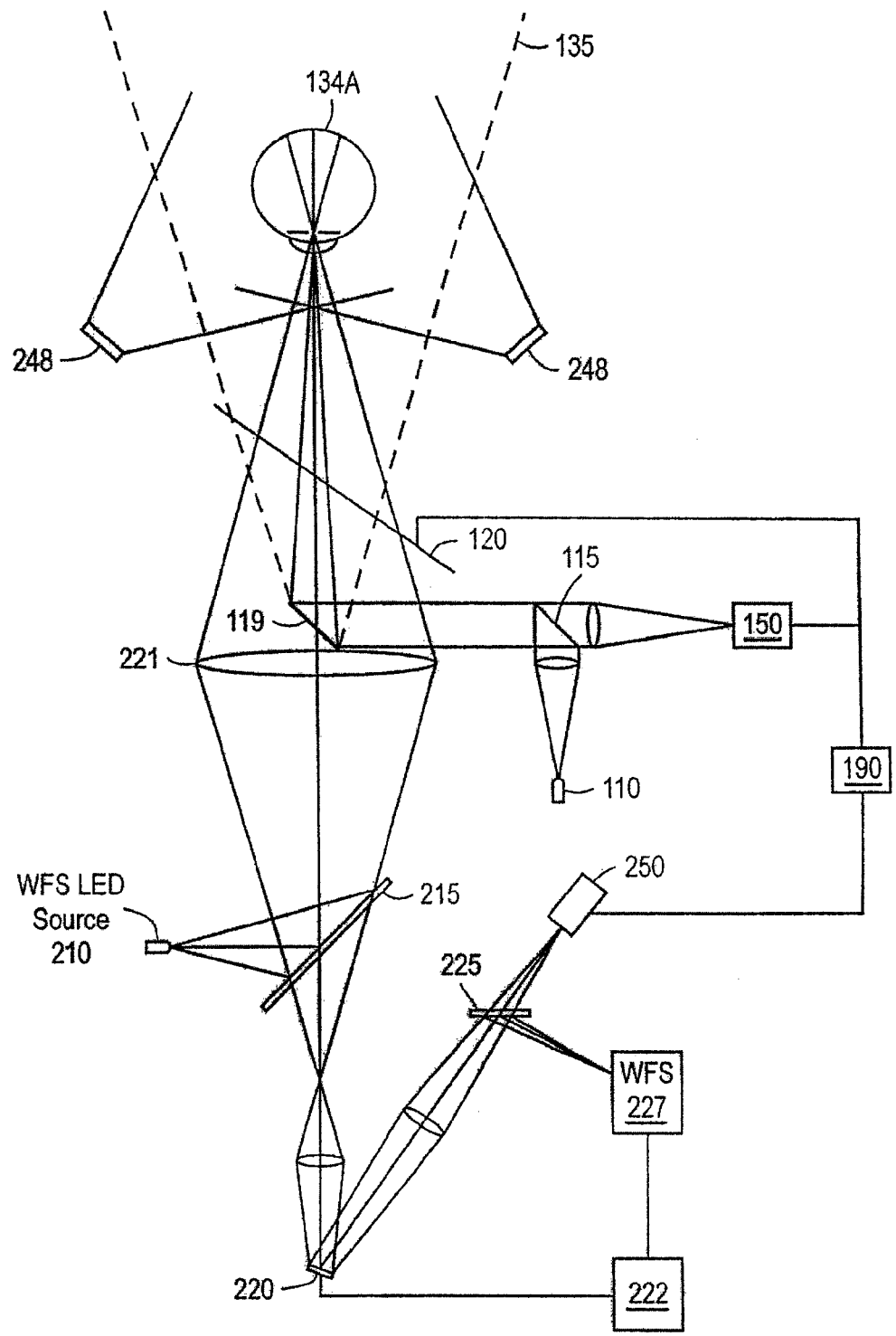
FIG. 2 is an illustration of another iris imaging system according to the present invention, based on retro-reflection from the eye.

FIG. 2 is an illustration of an example iris imaging system according to the present invention, based on retro-reflection from the eye. In this example, the acquisition subsystem 100 includes a light source 110, a beam splitter 115, a small "pickoff" mirror 119 and a camera 150. The imaging subsystem 200 includes a light source 210, a beamsplitter 215, a deformable mirror 220, a beamsplitter 225, a wavefront sensor 227 and a controller 222. It also includes a light source 248 and a camera 250. For convenience, the various light sources may be referred to as the acquisition light source 110, the WFS light source 210 and the iris imaging light source 248, respectively, to distinguish them from each other. The iris imaging system also includes a coarse tip-tilt steering mirror 120 controlled by controller 190, which is used as part of both the acquisition subsystem 100 and the imaging subsystem 200. In FIG. 2, the steering mirror 120 is depicted as a line through the optical beam but, for simplicity, reflection off the steering mirror is not shown (i.e., the optical path is unfolded with respect to steering mirror 120). Various lenses (or other optics) are used to collimate, focus, image or otherwise relay the optical beams throughout the system.

The acquisition subsystem 100 operates as follows. The acquisition light source 110 is the illumination for camera 150. Light produced by light source 110 reflects off beamsplitter 115, and mirror 119. Beamsplitter 115 separates light produced by source 110 that is exiting the system and light returning to the system to be imaged onto camera 150. Beamsplitter 115 could be a polarizing beamsplitter, which together with a quarterwave plate could be used to suppress back reflection and specular reflections. Beamsplitter 115 could also be a neutral beamsplitter (i.e., without polarization selectivity) for low cost and simplicity. Mirror 119 combines the optical paths of the acquisition subsystem 100 and the imaging subsystem 200 so they are generally aligned along a common optical axis. In this example, the two subsystems operate at different wavelengths, so mirror 119 is a dichroic beamsplitter that reflects the wavelengths of the acquisition subsystem 100 and passes the wavelengths of the imaging subsystem 200. The outgoing illumination from light source 110 then reflects off coarse steering mirror 120 to illuminate the acquisition subsystem 100's wider field of view 135. The field of view 135 may stare across the entire capture volume 50 or may be scanned across the capture volume. In this example, the field of view 135 is not wide enough to cover the entire capture volume in a staring mode. Rather, it is scanned across the capture volume by steering mirror 120. Subjects within the field of view 135 are represented by eyes 134, which are illuminated by the acquisition light source 110.

Eyes 134 within the field of view 135 retro-reflect light back to the coarse steering mirror 120, which directs the light to camera 150 via mirror 119 and beamsplitter 115. Camera 150 is a wide angle camera used to identify the general locations of eyes 134. In one implementation, the camera 150 is an electronic image sensor such as a CCD that periodically records discrete images of field of view 135. In one approach, the camera 150 records rapid sequences of images to monitor the movement of objects 134 within the field of view 135. The signals from the wide angle camera are analyzed by software (e.g., contained in controller 190) to identify eyes, which appear as bright circular spots due to the retro-reflections from the eyes 134. The camera 150 operates at the same wavelength as the illuminating source 110. Wavelength filters can be used to reject ambient light on the return optical path, while passing the illuminating wavelength. In addition, the light source 110 can be strobed. Synchronisation of the camera 150 exposures with the source 110 strobing can also increase the isolation between imaging and guiding (or wavefront sensor) cameras. Such synchronization can also reduce the effects of background light contamination.

Once eyes 134 are identified, the controller 190 determines a plan for imaging the irises. Preferably, iris images of both eyes are captured (although not necessarily simultaneously), in order to increase the accuracy of identification. In FIG. 2, the iris 134A is being imaged. If necessary, the controller 190 directs the coarse steering mirror 120 to bring the eye of interest 134A within the narrower field of view for the imaging subsystem 200. As drawn in FIG. 2, the coarse steering mirror 120 also steers the wide field of view 135 for the acquisition subsystem 100, although this is not required. One advantage of steering the acquisition subsystem 100 and imaging subsystem 200 together is that a fixed relationship between the wavefront sensor 227 and the acquisition camera 150 is maintained.

The imaging subsystem 200 operates as follows. WFS light source 210 illuminates the eye 134A. Light produced by light source 210 reflects off beamsplitter 215, propagates through lens system 221 and mirror 119, and is directed by steering mirror 120 to the eye 134A. Since this light is coming from the imaging subsystem 200, it has a narrower field of view than the field of view 135 of the acquisition subsystem. A portion of the illuminating light enters the eye 134A, which retro-reflects light back along the same path 120-221. The return light passes through the beamsplitter 215, reflects off deformable mirror 220 and is directed by beamsplitter 225 to the wavefront sensor 227. The wavefront sensor 227, controller 222 and deformable mirror 220 form an adaptive optics loop that is driven based on the retro-reflected light from the eye 134A.

In one variation, polarization is used to distinguish retro-reflected light from a target eye 134 from glints. The illuminating light from WFS light source 210 is polarized and beamsplitter 215 is a polarization beamsplitter. The beamsplitter 215 reflects the originally polarized light, directing it to the eye 134. A quarterwave plate placed after beamsplitter 215 (e.g., between beamsplitter 215 and lens 221) rotates the polarization by ninety degrees after a double pass (i.e., one pass upon transmission from the WFS light source 210 to the eye 134A and a second pass upon retro-reflection from the eye 134A). Glints, i.e., reflections from smooth surfaces, generally preserve the polarization of the incident light and therefore will be reflected by the polarization beamsplitter 215 on the return path and will not pass through to the wavefront sensor 227. Such glints may include reflections from the objective lens 221, reflections from the front of the eye 134 or glasses, and others. The retro-reflection from the retina of the target eye 134, however, does not maintain the polarization of the incident light due to the structure of the eye, and therefore a portion of this light is transmitted through the beamsplitter to the wavefront sensor 227.

While adaptive optics can be used in many applications to correct for high order aberrations, in this case, the adaptive optics loop is used mainly for fast tracking of the eye 134A (i.e., correction of tip/tilt errors in the wavefront) and preferably also for focus correction. This keeps the iris 134A within the narrow field of view of camera 250 and also focuses the camera (if focus correction is implemented). In this example, the light source 210 does not provide the primary illumination for camera 250. Rather, additional light sources 248 (i.e., the iris imaging light sources) provide off-axis illumination of the irises 134 for camera 250. For example, LEDs in the near infrared wavelength range can be used. The protective pigment melanin is more transparent at longer wavelengths. Thus, the details of the iris structure are more easily seen in heavily pigmented eyes by using light sources of these wavelengths. Alternatively, any other light source could be used that conforms to safety limits. The off-axis illumination generally results in higher contrast and fewer artifacts. Off-axis illumination angle also effects positioning of glints which can be deleterious to the identification accuracy. Glints can also be reduced by using polarized illumination with polarizing filters for the iris camera 250. In alternate approaches, illumination for camera 250 can be provided by ambient lighting, visible or infrared flash, or combinations of these.

Traditional adaptive optics systems, such as those developed for astronomy, may be too large, complex and/or costly to be effectively used in applications such as iris imaging. However, recent advances by AOptix Technologies of Campbell, Calif., have resulted in the development of complete adaptive optics systems, including electronics, that achieve sizes smaller than a shoe box. The AOptix adaptive optics systems require less than 25 W of power and can reliably operate unattended for extended periods of time. The small size, weight and power and high reliability of the AOptix adaptive optics systems make them suitable for applications such as the iris imaging applications described herein.

In these more compact systems, the deformable mirror 220 is a deformable curvature mirror based on applying different voltages across different areas of a piezoelectric material, thus causing deformation. Further details for this type of deformable mirror are described and shown in U.S. Pat. No. 6,464,364, "Deformable Curvature Mirror," filed Jan. 25, 2001 and issued Oct. 15, 2002, by J. Elon Graves and Malcolm J. Northcott; U.S. Pat. No. 6,568,647, "Mounting Apparatus for Deformable Mirror," filed Jan. 25, 2001 and issued May 27, 2003, by J. Elon Graves and Malcolm J. Northcott; and U.S. Pat. No. 6,721,510, "Atmospheric Optical Data Transmission System," filed Jun. 16, 2001 by J. Elon Graves and Malcolm J. Northcott. Furthermore, the wavefront sensor 227 is a wavefront curvature sensor based on defocused pupil images. Further details for this type of wavefront curvature sensor are described and shown in U.S. Pat. No. 6,452,145, "Method and Apparatus for Wavefront Sensing," filed May 26, 2000 and issued Sep. 17, 2002, by J. Elon Graves and Malcolm J. Northcott; and U.S. Pat. No. 6,721,510, "Atmospheric Optical Data Transmission System," filed Jun. 16, 2001 by J. Elon Graves and Malcolm J. Northcott. All of the foregoing are incorporated herein by this reference.

In one embodiment, the iris imaging system of FIG. 2 is designed for use in airport hallways, customs checkpoints, public transportation stations, secure building lobbies, and the like. Standoff distances of up to at least 10 meters would enable the scanning of a large room or hallway to identify the occupants. For example, a device could be placed in the vicinity of the departure and/or arrival screen in an airport. The system would then be able to identify anyone attempting to read the screen contents.

For this specific design, the acquisition subsystem 100 has a field of view 135 of approximately 12 degrees, resulting in a capture volume 50 measuring approximately 2 m×2 m×2 m at a 10 m range (without scanning). The acquisition light source 110 is a light-emitting diode (LED) having a wavelength in the range of 750 to 980 nm. Shorter wavelengths give better sensor quantum efficientcy, but wavelengths longer than approximately 890 nm are required for invisible operation. Longer wavelengths are also possible but require more expensive (not silicon) detectors. LED sources are generally preferred. Laser sources are problematical due to eye safety considerations, but could be used with careful engineering. Gas discharge lamps could also be used under some circumstances. Thermal sources such as tungsten lights and arc lamps could also be used but would be inefficient due to the requirement for wavelength filtering.

In this specific design, the illuminating wavelength used by the acquisition subsystem 100 is different than that used by the imaging subsystem 200, so mirror 119 can be wavelength-selective to separate the light for the acquisition subsystem 100 from that for the imaging subsystem. The acquisition camera 150 is an infrared enhanced monochrome TV camera with a resolution of approximately 720×500 pixels. The camera 150 operates at a 30 Hz frame rate.

With respect to the imaging subsystem 200, the resolution requirements drive the design of the iris imaging system 200. Consider a resolution requirement of 75 microns per pixel. Assuming diffraction limited performance, the required aperture diameter d is given by $d=\lambda z/r$, where z is the standoff distance and r is the required resolution. For example, assuming $\lambda=0.82\,\mu m$, and $z=10\,m$, the required aperture is 11 cm. As another example, a 100 µm resolution can be achieved at a visible wavelength of 0.5 µm at a 10 m standoff distance with a diffraction limited 5 cm aperture. However, infrared wavelengths are generally preferred for iris imaging due to the enhanced contrast observed at longer wavelengths.

The diffraction limited resolution requirement and large aperture also lead to a limited depth of field. If the geometric image spread due to focus depth of field is set to be less than half of the diffraction limit, then the depth of field l is given by $l=r^2/\lambda$. The 0.82 µm example yields a depth of field of approximately 7 mm. The 0.5 µm example yields a depth of field of approximately 2 cm. Depth of fields on the order of a few millimeters or a few centimeters makes focusing on moving objects difficult. Hence, it is advantageous for the adaptive optics loop to implement fast focus correction as well as fast tracking. With the adaptive optics augmented iris imaging system, images can be taken within a few milliseconds of identifying a target. Thus, the use of adaptive optics can increase the speed and accuracy of image capture for applications involving uncooperative targets.

Focus adjustment can also be achieved using other variations and approaches. For example, a variable focus lens or deformable mirror can be used to adjust the focus. Electromechanical lens position adjustment, movement of the camera 250 and use of a variable refractive index element are alternate ways to adjust focus. In addition, focus wavefront sensing can be based on image contrast measurements and dithering, or by use of a dedicated focus wavefront sensor, or by measuring the distance to the eye using time of flight of an optical or acoustic pulse.

Continuing with the specific example described above, the WFS light source 210 used in the iris imaging system 200 can be chosen to illuminate the eye so that the target individual is unaware of the process. LEDs having wavelengths in the range of 750 to 980 nm are generally preferred (and greater than approximately 890 nm for invisible operation), but other sources can be used as described above. Filling the telescope aperture with the illumination light as shown in FIG. 2 is advantageous, since it ensures that the pupil is fully illuminated by the eye reflection. The iris imaging light sources 248 are also preferably LEDs. Iris imaging standards currently specify wavelengths around the 850 nm range.

In this example, the WFS illuminating wavelength (used by the wavefront sensor 227) is also selected to be different from the illumination used to image the irises by camera 250. Hence, the beamsplitter 225 is dichroic to increase efficiency. However, these separations in wavelength are not required. The different beams can be separated using other techniques. For example, the iris imaging illumination and WFS illumination can be distinguished by time instead. The WFS LED 210 can be flashed synchronously with a WFS chopper (not shown in FIG. 2), and the iris imaging illumination 248 flashed to fill the dead time when the wavefront sensor 227 is not integrating signal. The iris imaging camera 250 preferably is a high quality monochrome imager. Due to the high speed tracking, this imager 250 can have a relatively small number of pixels, for instance a standard 640×480 video imager is convenient. For the iris imaging camera 250, high quality, high quantum efficiency and low signal to noise are relatively more important than resolution. The acquisition camera 150 will generally have a separate illumination system 110. If interference occurs between the acquisition illumination 110, the iris imaging illumination 248 and/or the fine tracking illumination 210, various techniques can be used to provide isolation, including for example techniques based on wavelength, polarization, temporal separation and/or angular or spatial separation.

Figure 3:
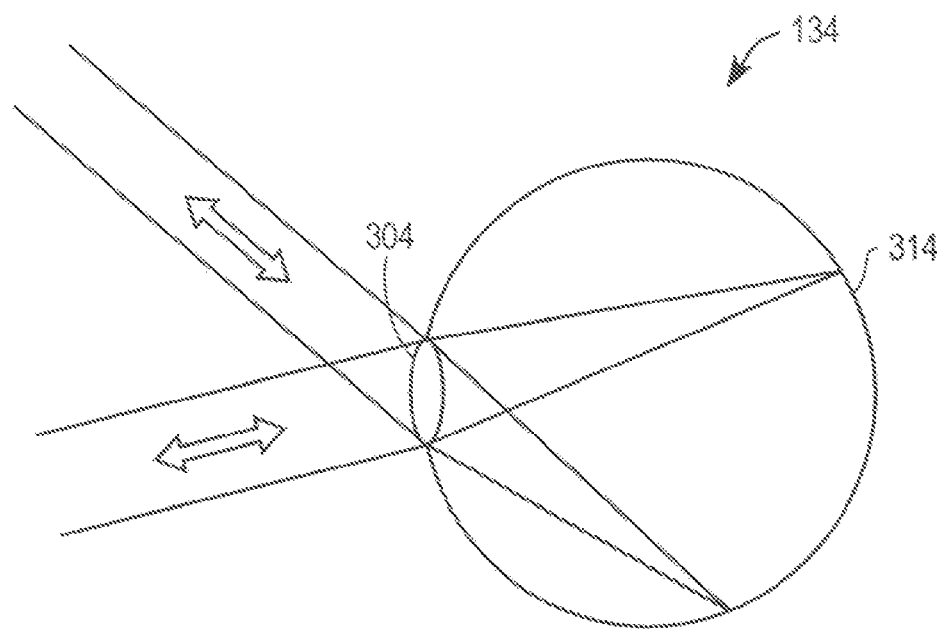
FIG. 3 is an illustration of retro-reflection from the eye.

The example of FIG. 2 is based on retro-reflection from the eye. FIG. 3 is an illustration of retro-reflection from the human eye. The intrinsic geometry of the eye causes it to act as a retro-reflector. Light that enters the eye lens 304 is focused onto the retina 314. Any light scattered by the retina back towards the lens 404 retraces its path out of the eye. Because the retina is in the focal plane of the eye lens, light is strongly directed in the backscatter direction. As FIG. 3 shows, light enters the eyeball through the pupil and reflects from the back curved surface of the retina 314. It is this back-reflection from the retina 314 that can be used to drive the fine tracking system in the imaging subsystem (e.g., the wavefront sensor in the adaptive optics loop). Also, the illustration of FIG. 3 shows that the illumination need not come from a face-on aspect to create a retro-reflection. Thus, the subject need not stare directly into the iris imaging camera for the acquisition and imaging system to work.

Figure 4:
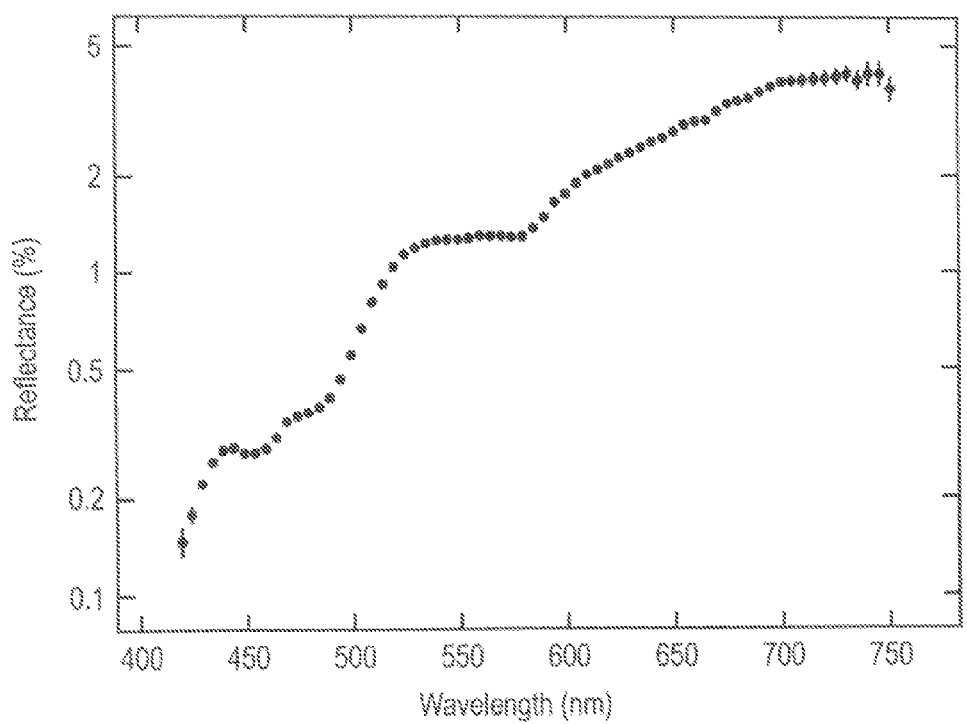
FIG. 4 is an illustration of a typical reflectance spectrum of a human eye.

FIG. 4 is an illustration of a typical reflectance spectrum of a human eye. This graph was originally presented in the thesis of Niels Zagers, University of Utrecht. The reflectance shows a strong peak towards the infrared. Using a wavelength of 750 nm (CD read laser wavelength), a reflectivity of 4% of the white Lambertian diffuser value is expected. The back reflection property is stronger in the red and near IR (around 800 nm) wavelengths, since melanin which is found in the retina, is less absorbing at red wavelengths. At a 750 nm or longer wavelength, the subject would only see faint illumination since this is outside the nominal visible region. At 880 nm or longer wavelength the light source will be essentially invisible.

The following example demonstrates how retro-reflected light from an eye 234 can be used in closed loop operation of an adaptive optics system. A subject at a 10 m distance can be illuminated with 0.1 mW of power to the eye, which is well within the eye safety limit. In this example, the retro-reflected light is expected to be approximately $6.4 \times 10^{-13}$ W/cm$^2$. Assuming a 5 cm imaging lens is used to achieve a 100 micron resolution, approximately $1.2 \times 10^{-11}$ W is captured on the wavefront sensor. This corresponds to a photon flux of approximately $5 \times 10^7$ photons per second. In one embodiment, a low order adaptive optics system running at a relatively slow rate is used. For example, a 19 actuator adaptive optics system updated at 1 KHz, provides approximately 2500 photons per actuator per update. A CCD type detector with better than 50-electron read noise and 50% quantum efficiency will provide sufficient signal to noise ration for closed loop operation of the adaptive optics system. For comparison, better than 10-electron read noise and 90% quantum efficiency is routinely achieved for scientific grade CCD imaging. Thus, the retro-reflected light can be used to derive the feedback signal to support adaptive optics-assisted fine tracking and imaging.

Advantages of using the eye as a retro-reflector to drive the wavefront sensor include low cost and long range. The low cost is due to the ability to use an inexpensive silicon detector as the wavefront sensor and inexpensive LEDs as light sources. An adequate signal is achieved even at long ranges due to the strong directionality of the retro-reflection. However, the retinal retro-reflection does not appear as a point source, so higher dynamic range detectors are used to generate an accurate wavefront signal.

Figure 5:
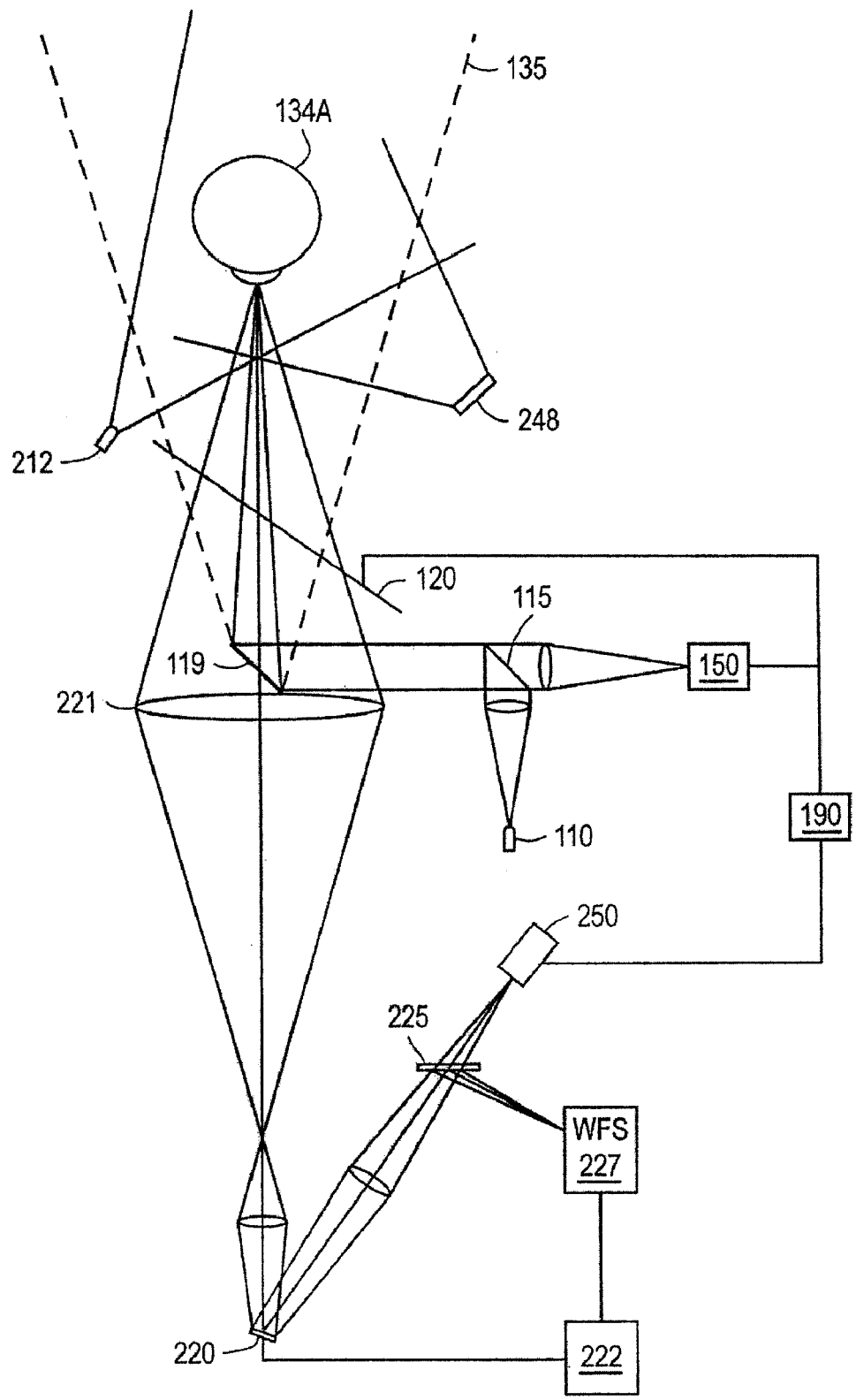
FIG. 5 is an illustration of another iris imaging system according to the present invention, based on glint from the eye.

In the example of FIG. 2, the reflection from the eye was a retinal retro-reflection. Alternatively, the front surface of the eye acts as a partial mirror with about 4% reflectivity. Reflections from this surface form a glint that can be used to steer the imaging subsystem 200 instead of the retro-reflection. For example, the system of FIG. 2 can be modified so that the light source 210 illuminates eye 134A, but the wavefront sensor 227 is driven by a glint reflection from the eye rather than a retro-reflection. Since glints can be produced by off-axis illumination, the light source 210 can be moved off-axis or even outside the telescope 221 for the imaging subsystem 200. In the example of FIG. 5, the light source 210 is replaced by an external light source 212. This source 212 is positioned at locations more like illuminators 248 but still produces a glint for telescope 221. In addition, the glint looks like a de-magnified image of the light source, so it tends to be more like a point source. A resulting advantage is that the size and shape of the glint is not a strong function of the distance to the subject.

One advantage of driving the wavefront sensor from the glint of the eyeball is that there is no limitation on distance over which glints from eyeballs can be used. Also, a point-like source does not require a wavefront sensor with a high dynamic range. However, glints return less light than retro-reflections from eyes, so more wavefront sensor sensitivity or a higher illumination flux may be required.

Although the details description contains many specifics, these should not be construed as limiting the scope of the invention but merely as illustrating different examples and aspects of the invention. It should be appreciated that the scope of the invention includes other embodiments not discussed in detail above. Various other modifications, changes and variations which will be apparent to those skilled in the art may be made in the arrangement, operation and details of the method and apparatus of the present invention disclosed herein without departing from the spirit and scope of the invention as divined in the appended claims. For example, the fine tracking system within the imaging subsystem may use a deformable mirror to steer the camera from eye to eye, but the deformable mirror may be driven by feedback other than from a wavefront sensor. For example LIDAR, radar and other range finding technologies, image parallax or image contrast measurements and pattern recognition can be used to drive the deformable mirror. Therefore, the scope of the invention should be determined by the appended claims and their legal equivalents.

What is claimed is:

1. An iris imaging system comprising an imaging subsystem, the imaging subsystem comprising:
   a camera for capturing images of irises with sufficient resolution for biometric identification;
   a light source for producing light to illuminate eyes; and
   a fine tracking system comprising an adaptive optics loop including:
      a deformable mirror for adjusting a wavefront of an eye reflection of the light illuminating the eyes;
      a wavefront sensor for sensing the wavefront of the eye reflected light; and
      a controller coupled between the deformable mirror and the wavefront sensor, for adjusting the deformable mirror based on the sensed wavefront to steer a field of view of the camera to the eyes,
   wherein the fine tracking system can track irises to better than 0.5 cm accuracy.

2. The iris imaging system of claim 1 wherein the eye reflection comprises a retro-reflection from the eye.

3. The iris imaging system of claim 1 wherein the eye reflection comprises a glint reflection from the eye.

4. The iris imaging system of claim 1 wherein the imaging subsystem further comprises:
   a polarization beamsplitter positioned between the deformable mirror and the wavefront sensor, wherein the light source produces polarized light and the polarization beamsplitter combines the polarized light into an optical path with the deformable mirror but reflects return light of the same polarization away from the wavefront sensor.

5. The iris imaging system of claim 1 wherein the deformable mirror is a deformable curvature mirror based on applying different voltages across different areas of a piezoelectric material.

6. The iris imaging system of claim 1 wherein the wavefront sensor is a wavefront curvature sensor based on defocused pupil images.

7. The iris imaging system of claim 1 wherein the fine tracking system has a speed to acquire and image at least ten irises per second.

8. The iris imaging system of claim 1 wherein the light source produces non-laser light.

9. The iris imaging system of claim 1 wherein the light source is an LED.

10. The iris imaging system of claim 1 wherein the light source produces light in a wavelength range that is greater than 750 nm.

11. The iris imaging system of claim 1 wherein the light source produces light in a wavelength range of 750 nm to 980 nm.

12. The iris imaging system of claim 1 wherein the light source produces light in a wavelength range that is greater than 850 nm.

13. The iris imaging system of claim 1 wherein the light source produces light in a wavelength range that is not visible to humans.

14. The iris imaging system of claim 1 wherein the camera is a monochromatic camera.

15. The iris imaging system of claim 1 wherein the camera captures images of irises with a resolution of 200 microns or better.

16. The iris imaging system of claim 1 wherein the camera captures images of irises with a resolution of 100 microns or better.

17. The iris imaging system of claim 1 wherein the camera captures images of irises with a resolution of 75 microns or better.

18. The iris imaging system of claim 1 further comprising:
   off-axis light sources for illuminating the irises for image capture by the camera.

19. The iris imaging system of claim 1 wherein the imaging subsystem can cover a capture volume of at least 1 cubic meter.

20. The iris imaging system of claim 1 wherein the camera can capture iris images at a standoff of at least 5 m.

21. The iris imaging system of claim 1 wherein the camera can capture iris images at a standoff of at least 10 m.

22. The iris imaging system of claim 1 further comprising:
   an acquisition subsystem for identifying an approximate location of subjects within a capture volume; and
   a controller coupled to the acquisition subsystem and the imaging subsystem for coordinating the two subsystems.

23. The iris imaging system of claim 22 wherein the acquisition subsystem identifies the approximate location of subjects based on an eye reflection of illuminating light from the subjects' eyes.

24. The iris imaging system of claim 22 wherein the acquisition subsystem stares at the entire capture volume.

25. The iris imaging system of claim 22 wherein the acquisition subsystem scans across the capture volume.

26. The iris imaging system of claim 22 wherein the acquisition subsystem and the imaging subsystem are aligned along a common optical axis.

27. An iris imaging system comprising an imaging subsystem, the imaging subsystem comprising:
   a camera for capturing images of irises with sufficient resolution for biometric identification;
   a light source for producing light to illuminate eyes; and
   a fine tracking system comprising an adaptive optics loop for steering a field of view of the camera to the eyes and also for focusing the camera on the irises, based on an eye reflection of the light illuminating the eyes, wherein the fine tracking system can track irises to better than 0.5 cm accuracy.

28. The iris imaging system of claim 27 wherein the eye reflection comprises a retro-reflection from the eye.

29. The iris imaging system of claim 27 wherein the eye reflection comprises a glint reflection from the eye.

30. The iris imaging system of claim 27 wherein the adaptive optics loop comprises a deformable mirror that is adjusted to steer the field of view of the camera to the eyes and also to focus the camera on the irises, based on a wavefront of the eye reflected light.

31. The iris imaging system of claim 30 wherein the deformable mirror is a deformable curvature mirror based on applying different voltages across different areas of a piezoelectric material.

32. The iris imaging system of claim 27 wherein the adaptive optics loop further comprises a wavefront curvature sensor based on defocused pupil images.

33. The iris imaging system of claim 27 wherein the fine tracking system has a speed to acquire and image at least ten irises per second.

34. The iris imaging system of claim 27 wherein the light source produces non-laser light.

35. The iris imaging system of claim 27 wherein the light source is an LED.

36. The iris imaging system of claim 27 wherein the light source produces light in a wavelength range that is greater than 750 nm.

37. The iris imaging system of claim 27 wherein the light source produces light in a wavelength range of 750 nm to 980 nm.

38. The iris imaging system of claim 27 wherein the light source produces light in a wavelength range that is greater than 850 nm.

39. The iris imaging system of claim 27 wherein the light source produces light in a wavelength range that is not visible to humans.

40. The iris imaging system of claim 27 wherein the camera is a monochromatic camera.

41. The iris imaging system of claim 27 wherein the camera captures images of irises with a resolution of 200 microns or better.

42. The iris imaging system of claim 10 wherein the camera captures images of irises with a resolution of 100 microns or better.

43. The iris imaging system of claim 27 wherein the camera captures images of irises with a resolution of 75 microns or better.

44. The iris imaging system of claim 27 further comprising: off-axis light sources for illuminating the irises for image capture by the camera.

45. The iris imaging system of claim 27 wherein the imaging subsystem can cover a capture volume of at least 1 cubic meter.

46. The iris imaging system of claim 27 wherein the camera can capture iris images at a standoff of at least 5 m.

47. The iris imaging system of claim 27 wherein the camera can capture iris images at a standoff of at least 10 m.

48. The iris imaging system of claim 27 further comprising:
an acquisition subsystem for identifying an approximate location of subjects within a capture volume; and
a controller coupled to the acquisition subsystem and the imaging subsystem for coordinating the two subsystems.

49. The iris imaging system of claim 48 wherein the acquisition subsystem identifies the approximate location of subjects based on an eye reflection of illuminating light from the subjects' eyes.

50. The iris imaging system of claim 48 wherein the acquisition subsystem stares at the entire capture volume.

51. The iris imaging system of claim 48 wherein the acquisition subsystem scans across the capture volume.

52. The iris imaging system of claim 48 wherein the acquisition subsystem and the imaging subsystem are aligned along a common optical axis.

53. A method for imaging an iris of and eye, comprising:
illuminating the eye with light;
sensing a wavefront of an eye reflection from the eye;
steering a field of view of a camera to the eye and focusing the camera on an iris of the eye, based on the wavefront of the eye-reflected light; and
the camera capturing an image of the iris with at least 200 micron resolution for biometric identification.

54. The method of claim 53 wherein the eye reflection comprises a retroreflection from the eye.

55. The method of claim 53 weherein the eye reflection comprised a glint reflection from the eye.

56. The method of claim 53 wherein the stop of steering a field of view of the camera to the eye comprises using an adaptive optics loop based on the eye reflected light to steer the field of view of the camera to the eye.

57. The method of claim 53 wherein the step of steering a field of view of the camera to the eye is capable of steering the field of view of the camera to at least ten eyes per second.

58. The method of claim 53 wherein the step of illuminating the comprises illuminating the eye with light in a wavelength range that is greater than 750 nm.

59. The method of claim 53 wherein the step of illuminating the eye comprises illuminating the eye with light in a wavelength range that is not visible to humans.

60. The method of claim 53 wherein the field of view of the camera can be steered to cover a capture volume of a least 1 cubic meter.

61. The method of claim 53 wherein the camera can capture iris images at a standoff of at least 5m.

62. The method of claim 53 further comprising:
identifying an approximate location of subjects within a capture volume; wherein the step of steering the field of view of the camera to the eye is based in part on the identified approximate locations.

63. The method of claim 62 wherein the step of identifying the approximate location of subjects is based on an eye reflection of illuminating light from the subjects' eyes.

64. The method of claim 62 wherein the step of identifying the approximate location of subjects comprises staring at the entire capture volume.

65. The method of claim 62 wherein the step of identifying the approximate location of subjects comprises scanning across the capture volume.

* * * * *

UNITED STATES PATENT AND TRADEMARK OFFICE
CERTIFICATE OF CORRECTION

PATENT NO.           : 7,428,320 B2
APPLICATION NO. : 11/297578
DATED                    : September 23, 2008
INVENTOR(S)         : Malcolm J. Northcott and J. Elon Graves It is certified that error appears in the above-identified patent and that said Letters Patent is hereby corrected as shown below:

On the Title Page, item (75), line 1; add period after middle initial "J" of first inventor: Malcolm J. Northcott.

Column 13, Claim 42, line 1, change -- claim 10 -- to "claim 27".

Column 14, Claim 55, line 2, change -- comprised -- to "comprises".

Column 14, Claim 58, line 2, add the word "eye" so that the line reads "...the eye comprises illuminating the eye...".

Signed and Sealed this

Twenty-second Day of December, 2009

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,428,320 B2 | Page 1 of 1 |
| APPLICATION NO. | : 11/297578 | |
| DATED | : September 23, 2008 | |
| INVENTOR(S) | : Malcolm J. Northcott and J. Elon Graves | |

It is certified that error appears in the above-identified patent and that said Letters Patent is hereby corrected as shown below:

On the Title Page, item (75), line 1; add period after middle initial "J" of first inventor: Malcolm J. Northcott.

Column 13, Claim 42, line 15, change -- claim 10 -- to "claim 27".

Column 14, Claim 55, line 12, change -- comprised -- to "comprises".

Column 14, Claim 58, line 22, add the word "eye" so that the line reads "...the eye comprises illuminating the eye...".

This certificate supersedes the Certificate of Correction issued December 22, 2009.

Signed and Sealed this

Twelfth Day of January, 2010

David J. Kappos
*Director of the United States Patent and Trademark Office*